US00PP36655P2

(12) United States Plant Patent
Meier

(10) Patent No.: US PP36,655 P2
(45) Date of Patent: May 6, 2025

(54) ***HAKONECHLOA* PLANT NAMED 'Hakbri2'**

(50) Latin Name: *Hakonechloa macra*
Varietal Denomination: Hakbri2

(71) Applicant: Gurjit Sidhu, Mission (CA)

(72) Inventor: Corey Meier, Centralia, WA (US)

(73) Assignee: Sidhu Gurjit, Mission (CA)

( * ) Notice: Subject to any disclaimer, the term of this patent is extended or adjusted under 35 U.S.C. 154(b) by 0 days.

(21) Appl. No.: 18/925,113

(22) Filed: Oct. 24, 2024

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Susan McCormick Ewoldt
*Assistant Examiner* — Zachariah Allan Kay
(74) *Attorney, Agent, or Firm* — Penny J. Aguirre

(57) ABSTRACT

A new and unique cultivar of *Hakonechloa* plant named 'Hakbri2' that is characterized by its variegated foliage that is dark to medium green in color with white to creamy white stripes.

2 Drawing Sheets

Botanical classification: *Hakonechloa macra.*
Varietal designation: 'Hakbri2'.

CROSS-REFERENCE TO A RELATED APPLICATION

This application is related to a Canadian plant breeders' rights application filed on Mar. 13, 2024, application No. 24-11628. The Applicant received the information for the Plant breeders' rights application directly from the Inventor.

BACKGROUND OF THE INVENTION

The present invention relates to a new and distinct cultivar of *Hakonechloa macra* and will be referred to hereafter by its cultivar name, 'Hakbri2'. 'Hakbri2' represents a new ornamental grass grown for landscape use.

The inventor discovered the new cultivar in summer of 2021 as a naturally occurring shoot mutation of *Hakonechloa macra* 'Aureola' (not patented) that was growing in a container in a production block in Elma, Washington.

Asexual propagation of the new cultivar was first accomplished by tissue culture using meristematic tissue in Elma, Washington in 2022 by the Inventor. Asexual propagation by tissue culture has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Hakbri2' as a unique cultivar of *Hakonechloa.*

1. 'Hakbri2' exhibits variegated foliage that is dark to medium green in color with white to creamy white stripes.

The female parent plant is similar to 'Hakbri2' in having foliage that is variegated. The female parent differs from 'Hakbri2' in having foliage that is variegated with stripes green and yellow in color. 'Hakbri2' can also be compared to the *Hakonechloa macra* cultivar 'Hakbri1' (U.S. Plant Pat. No. 34,999). 'Hakbri1' is similar to 'Hakbri2' in having variegated foliage. 'Hakbri1' differs from 'Hakbri2' in having foliage that is yellow in color with white and creamy white stripes, smaller in size, and less sun tolerant.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Briggs Nursery, Nursery Guide, Floral Daily, Garden Center Magazine, AIPH (Farwest Show), Horticulture Week, Digger Magazine, Greenhouse Grower, East Coast Nurseries, CBInsights (Walla Walla Nursery), Issuu, Queen Anne & Magnolia News, Portal Szolkarski, Verdant Yakima, Shonnard's Nursery, Dennis'7 Dees, Shop Settings, and The Canadian Food Inspection Agency.

BRIEF DESCRIPTION OF THE DRAWINGS

The accompanying color photographs illustrate the overall appearance and distinct characteristics of the new *Hakonechloa.* The photographs were taken of a 2-year-old plant of the new cultivar as grown in a 2-gallon container outdoors in Elma, Washington.

The photograph in FIG. 1 provides a side view of 'Hakbri2' in bloom.

Figure 1:
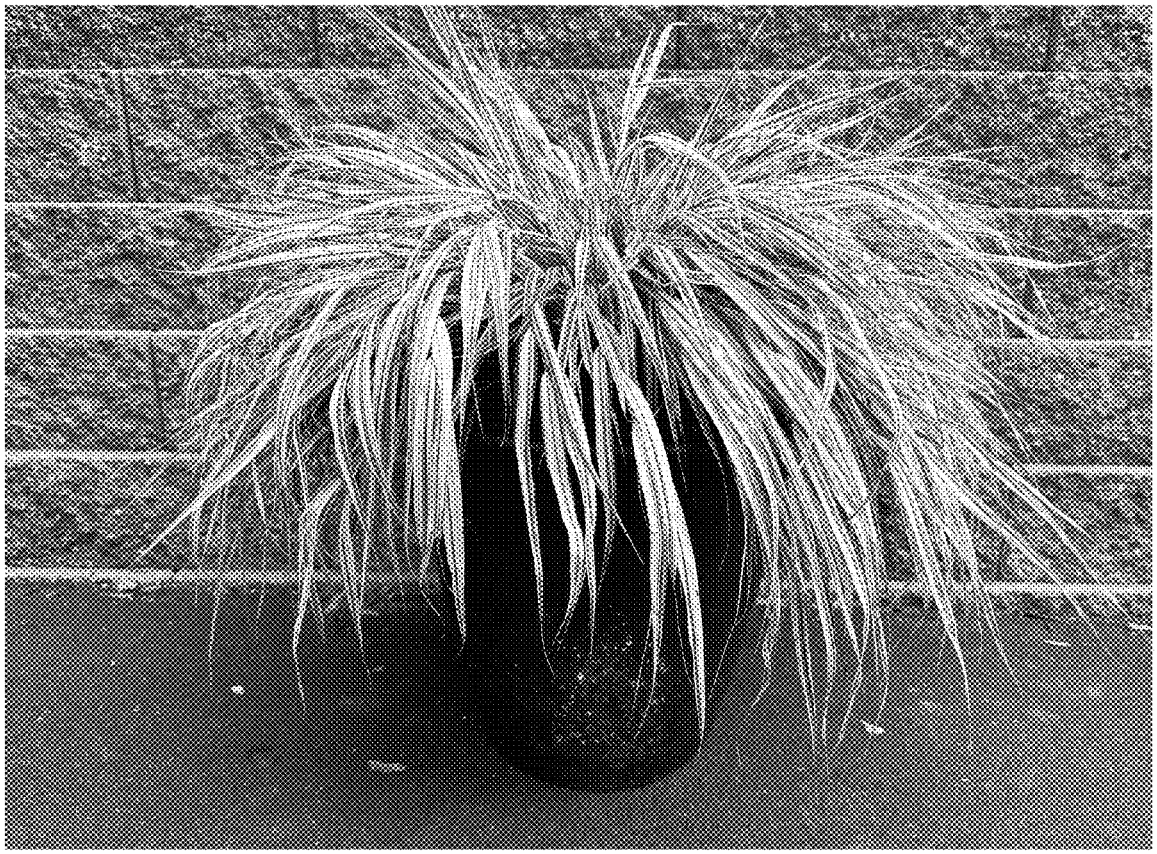
Figure 2:
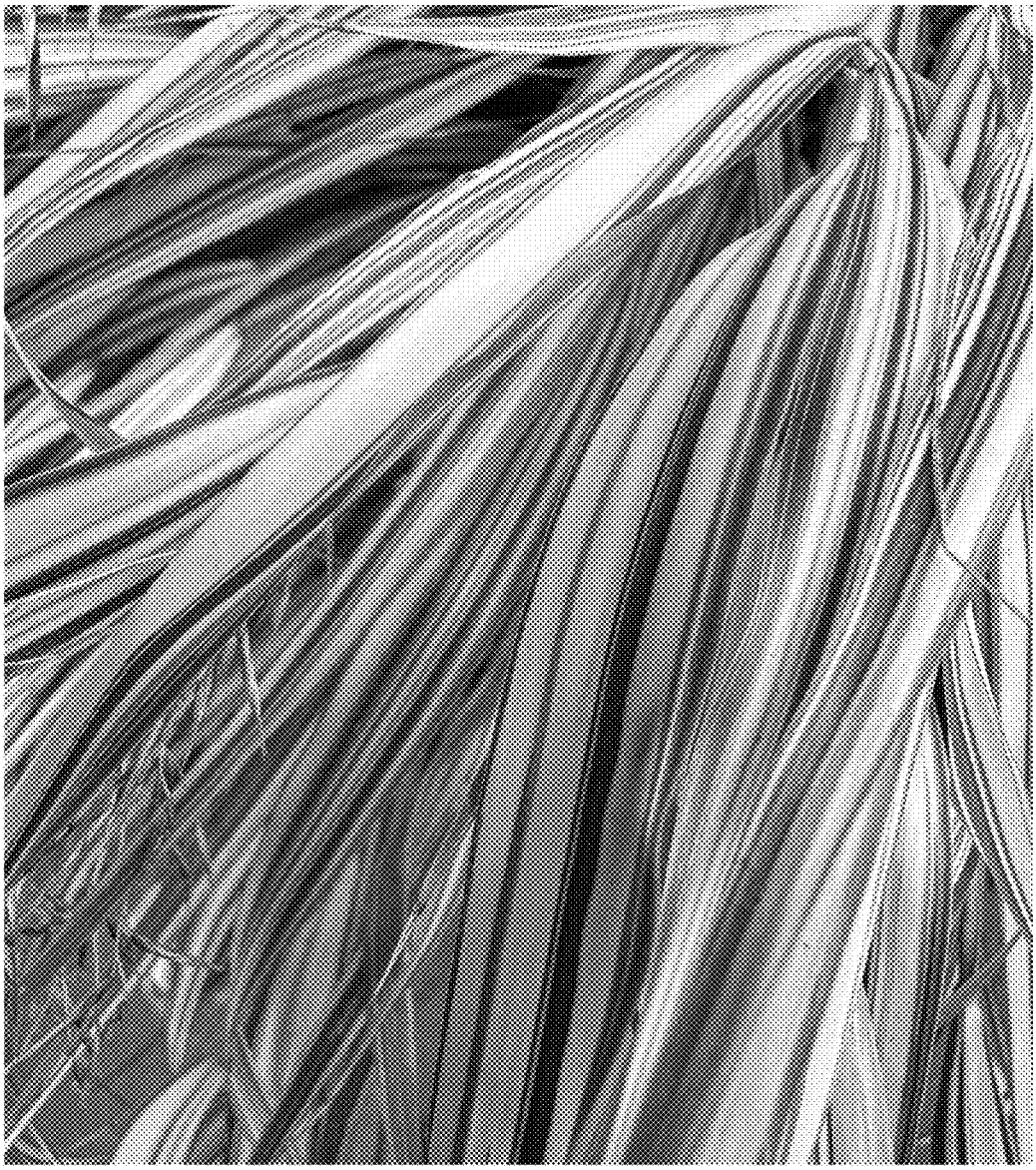

The photograph in FIG. 2 provides a close-up view of the foliage of 'Hakbri2'.

The colors in the photographs are as close as possible with the digital photography and printing techniques utilized and the color codes in the detailed botanical description accurately describe the new *Hakonechloa*.

BOTANICAL DESCRIPTION OF THE PLANT

The following is a detailed description of 2-year-old plants of 'Hakbri2' as grown outdoors in 2-gallon containers in Elma, Washington. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming habit.*—Late summer into early fall in Elma, Washington.

*Plant type.*—Herbaceous grass.

*Plant habit.*—Rounded, compact plant habit forming a low growing mound of cascading foliage.

*Height and spread.*—An average of 70 cm in spread and 25 cm in height as a 2-year-old plant in a container.

*Hardiness.*—At least in U.S.D.A. Zones 5 to 9.

*Diseases and pests.*—No susceptibility or resistance to diseases or pests has been observed.

*Root description.*—Fibrous, fine, and dense, N200A in color.

*Root development.*—Average of 4 weeks for root initiation and 5 to 6 months to produce a young plant in a liner.

*Propagation.*—Tissue culture.

*Growth rate.*—Vigorous to moderate.

Culm (stem) description:

*General.*—Round, sheathed.

*Culm color.*—158A, covered by leaf sheaths; 182B.

*Culm size.*—Average of 17 cm in length and 1 mm in width.

*Stem surface.*—Glabrous, satiny, glossy.

*Stem number.*—Average of 2,000.

*Internode length.*—Average of 3 cm.

*Branching.*—Basal branches only, no lateral branches.

Foliage description:

*Leaf shape.*—Lanceolate.

*Leaf division.*—Simple.

*Leaf base.*—Cuneate and decurrent at stem.

*Leaf apex.*—Acuminate-like but tapering to a very fine point.

*Leaf aspect.*—Cascading.

*Leaf venation.*—Parallel, matches leaf color.

*Leaf margins.*—Entire.

*Leaf attachment.*—Sheathed.

*Leaf size.*—Average of 16 cm in length, 1 cm in width, sheathed portion; an average of 2 cm in length and 1 mm in width.

*Leaf number.*—Average of 6 per culm.

*Leaf arrangement.*—Alternate.

*Ligule.*—None.

*Leaf surface.*—Both surfaces; matte, glabrous, translucent.

*Leaf color.*—Young and mature upper and lower surface; variegated, vertical streaks of 147A to 147B, NN155D, and 158C.

Inflorescence description:

*General description.*—Terminal airy panicle of single spikelets.

*Lastingness of inflorescence.*—Each panicle blooms for about 3 weeks, persistent.

*Fragrance.*—None.

*Panicle size.*—Average of 13 cm in length and up to 6 cm in width.

*Panicle number.*—One per culm.

*Rachis.*—An average of 8 cm in length (continuous with culm), 0.5 mm in diameter, 158D in color.

*Spikelet bud.*—Average of 8 mm in length and 1 mm in width, narrow lanceolate in shape, 148A.

*Spikelet description.*—Single floret enclosed by one glume and one lemma, glume; lanceolate in shape with a glabrous surface, entire margin, acute apex, 1.3 cm in length, 0.8 mm in diameter, color; 148A and 145C, randomly flushed with a blend of N187A and 187B, then turning to 166A as it matures, lemma; lanceolate in shape with a glabrous and glossy surface, entire margin, acute apex, 8 mm in length, 0.8 mm in width and 148A in color.

*Spikelet number.*—Average of 14 per panicle.

*Spikelet size.*—About 8 cm in length and 3 cm in width.

Reproductive organs:

*Stamens.*—2, anthers; dorsifixed, x-shaped, 2 mm in length, 158A in color, pollen; not observed.

*Pistils.*—2, 2.3 mm in length, stigmas; fimbriate in shape, 0.5 mm in length, and 158A in color, style; transparent in color, 0.5 mm in length, ovary; 148A in color.

*Seed.*—Seed development has not been observed.

It is claimed:

1. A new and distinct cultivar of *Hakonechloa* plant named 'Hakbri2' as herein illustrated and described.

* * * * *